(12) United States Patent
Cully et al.

(10) Patent No.: US 11,707,611 B2
(45) Date of Patent: Jul. 25, 2023

(54) IMPLANTABLE APPARATUS FOR RETENTION OF BIOLOGICAL MOIETIES

(71) Applicant: W. L. Gore & Associates, Inc., Newark, DE (US)

(72) Inventors: Edward H. Cully, Flagstaff, AZ (US); Paul D. Drumheller, Flagstaff, AZ (US); Jeffrey B. Duncan, Flagstaff, AZ (US); Nathan Friedman, Flagstaff, AZ (US)

(*) Notice: Subject to any disclaimer, the term of this patent is extended or adjusted under 35 U.S.C. 154(b) by 113 days.

(21) Appl. No.: 15/805,744

(22) Filed: Nov. 7, 2017

(65) Prior Publication Data

US 2018/0126133 A1    May 10, 2018

Related U.S. Application Data

(60) Provisional application No. 62/435,291, filed on Dec. 16, 2016, provisional application No. 62/419,130, filed on Nov. 8, 2016.

(51) Int. Cl.
*A61M 31/00*    (2006.01)
*A61F 2/02*    (2006.01)
*A61F 2/00*    (2006.01)

(52) U.S. Cl.
CPC ......... *A61M 31/002* (2013.01); *A61F 2/0077* (2013.01); *A61F 2/022* (2013.01); *A61F 2002/009* (2013.01); *A61F 2002/0081* (2013.01); *A61F 2210/0004* (2013.01); *A61F 2210/009* (2013.01); *A61F 2210/0014* (2013.01); *A61F 2210/0076* (2013.01); *A61F 2230/0004* (2013.01); *A61F 2230/0008* (2013.01); *A61F 2230/0013* (2013.01);
(Continued)

(58) Field of Classification Search
CPC ...... A61F 2230/0008; A61F 2230/0004; A61F 2230/0013; A61F 2230/0034; A61F 2210/0014; A61M 2205/0266
See application file for complete search history.

(56) References Cited

U.S. PATENT DOCUMENTS 5,476,589 A   12/1995   Bacino
5,773,286 A   6/1998   Dionne et al.
(Continued)

FOREIGN PATENT DOCUMENTS

CN   1527687   9/2004
CN   101883539   11/2010
(Continued)

OTHER PUBLICATIONS

International Search Report PCT/US2017/060499 dated Mar. 5, 2018.

*Primary Examiner* — Nathan R Price
*Assistant Examiner* — Anh Bui
(74) *Attorney, Agent, or Firm* — W. L. Gore & Associates, Inc.; Amy L. Miller

(57) ABSTRACT

An implantable containment apparatus for receiving and retaining a biological moiety or a therapeutic device within a tissue bed is disclosed. The device includes a shaping element to maintain the device in a generally toroidal configuration and to return the apparatus to that configuration after deformation. The apparatus can be placed in a host tissue with minimal trauma to the patient. Methods for implanting and using the apparatus are also disclosed.

25 Claims, 12 Drawing Sheets

(52) U.S. Cl.
CPC ............... *A61F 2230/0034* (2013.01); *A61F 2250/0031* (2013.01); *A61F 2250/0051* (2013.01); *A61F 2250/0068* (2013.01); *A61M 2202/09* (2013.01); *A61M 2202/203* (2013.01); *A61M 2202/206* (2013.01); *A61M 2205/0266* (2013.01); *A61M 2205/0272* (2013.01); *A61M 2205/04* (2013.01)

(56) References Cited

U.S. PATENT DOCUMENTS

| | | | |
|---|---|---|---|
| 5,787,900 | A * | 8/1998 | Butler ................... A61F 2/022 |
| | | | 604/890.1 |
| 5,814,405 | A | 9/1998 | Branca et al. |
| 5,843,069 | A | 12/1998 | Butler et al. |
| 5,897,955 | A | 4/1999 | Drumheller |
| 5,980,889 | A | 11/1999 | Butler et al. |
| 6,426,214 | B1 | 7/2002 | Butler et al. |
| 2005/0288783 | A1* | 12/2005 | Shaoulian ............ A61F 2/2448 |
| | | | 623/2.37 |
| 2006/0136049 | A1 | 6/2006 | Rojo |
| 2013/0131637 | A1* | 5/2013 | DiCesare ............ A61M 31/002 |
| | | | 604/285 |
| 2013/0296638 | A1 | 11/2013 | Deegan |
| 2015/0105859 | A1* | 4/2015 | Frigstad ............... A61F 2/0036 |
| | | | 623/14.13 |
| 2016/0045312 | A1* | 2/2016 | Braido ............... A61B 5/02028 |
| | | | 623/2.37 |
| 2016/0303365 | A1* | 10/2016 | Jadwizak ............... A61N 1/057 |
| 2017/0281827 | A1* | 10/2017 | Baker ................... A61L 27/306 |

FOREIGN PATENT DOCUMENTS

| | | |
|---|---|---|
| CN | 104398315 | 9/2011 |
| JP | 2002532135 | 10/2002 |
| JP | 2005194272 | 7/2005 |
| JP | 2005533554 | 11/2005 |
| JP | 2006326044 | 12/2006 |
| JP | 20078535387 | 12/2007 |
| JP | 2009504271 | 2/2009 |
| JP | 2009-511196 A | 3/2009 |
| JP | 2011529731 | 12/2011 |
| JP | 2013-514837 A | 5/2013 |
| WO | WO 93/00128 | 1/1993 |

* cited by examiner

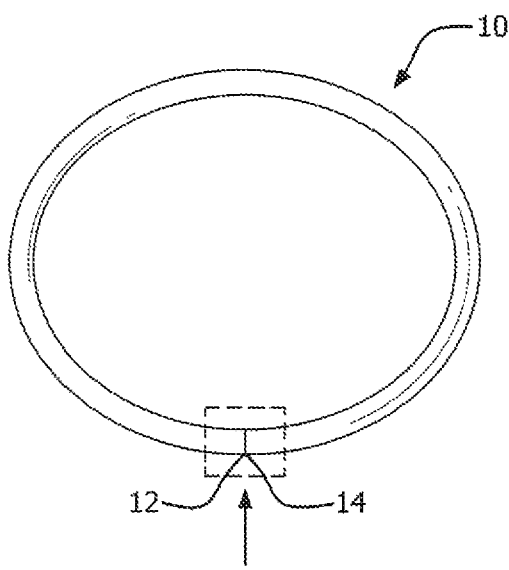
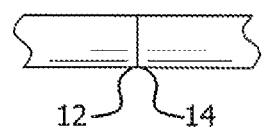
FIG. 1A
FIG. 1B
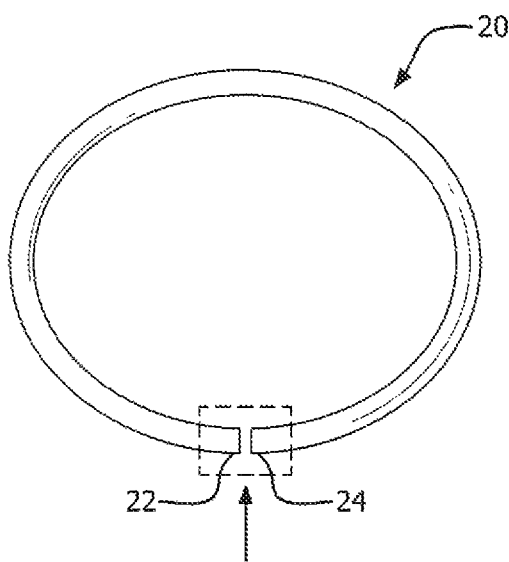
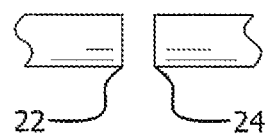
FIG. 2A
FIG. 2B

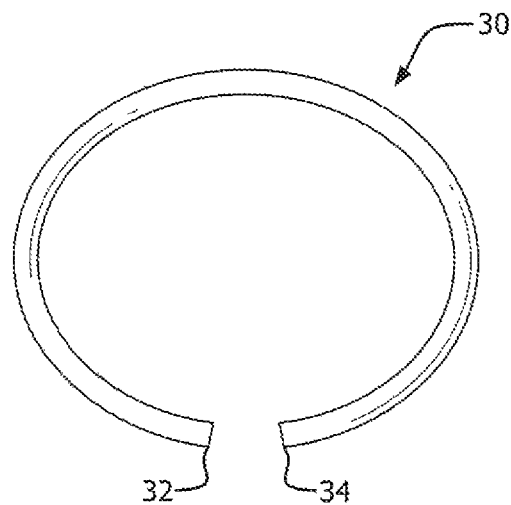
FIG. 3
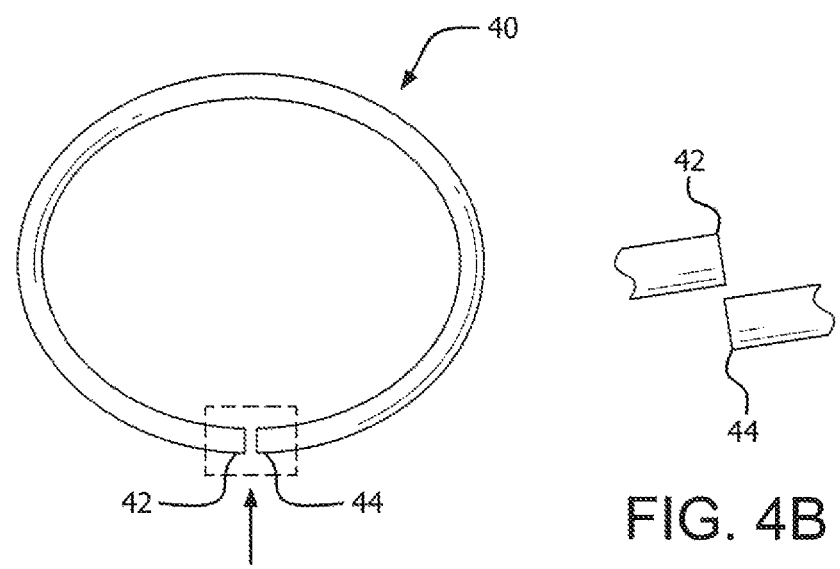
FIG. 4A
FIG. 4B

IMPLANTABLE APPARATUS FOR RETENTION OF BIOLOGICAL MOIETIES

FIELD

The present invention relates to the fields of implantable biological devices and biological therapies, and in particular, to a containment apparatus for housing biological moieties or devices for the retention of biological moieties.

BACKGROUND

Biological therapies are increasingly viable methods for treating peripheral artery disease, aneurysm, heart disease, Alzheimer's and Parkinson's diseases, autism, blindness, diabetes, and other pathologies.

With respect to biological therapies in general, cells, viruses, viral vectors, bacteria, proteins, antibodies, and other bioactive moieties may be introduced into a patient by surgical or interventional methods. Surgical techniques include, but are not limited to, blunt planar dissection into a tissue or organ. Interventional techniques include, but are not limited to, injection to a target site via catheter or needle. These methods cause trauma to host tissue, leading to unwanted inflammation, lack of vascularity, and immune reactions, all of which can reduce viability and efficacy of the biological moiety. The methods also can reduce the viability and efficacy of the biological moiety due to shearing forces experienced during transport through a fine-bore needle or catheter. And the increases in pressure caused by injection into a dense tissue can induce trauma. Implanted cells often do not engraft and can migrate from the injection site.

Devices for encapsulating biological moieties conventionally include a selectively permeable membrane to contain the therapeutic agent while remaining permeable to nutrients to sustain the agent, waste from the agent, and the therapeutic product produced by the agent. When implanted in a patient, the typical biological response by the patient to most of these therapeutic devices is the formation of a fibrotic capsule around the device. With most drug delivery and gene therapy devices, this can limit the performance of the device, particularly when the therapeutic agent has a short half-life. For cell encapsulation devices, a fibrotic capsule encasing the device most often deprives the encapsulated cells of life sustaining exchange of nutrients and waste products with tissues of a patient. The result is usually fatal to the encapsulated cells. Furthermore, a fibrotic capsule encasing a therapeutic device, usually makes surgical retrieval of the device difficult.

Other implantable devices include an external membrane that can support vascularization. That is, when certain therapeutic devices are implanted in a patient, predominantly vascular tissues of the patient can be stimulated to grow into direct, or near direct, contact with the device. On one hand, this is desirable because the therapeutic product of the device can then be delivered directly to the circulation of the patient through the vascular tissues that are in contact with the device. On the other hand, this is undesirable because once vascular tissues of a patient have grown in contact with one of these implantable therapeutic devices, removal of the device requires surgical dissection of the tissues to expose and remove the device. Surgical dissection of vascular tissues, particularly capillary tissue, can often be a difficult and painful procedure. Whether encased in a fibrotic capsule or surrounded with vascular tissue, the problem of retrieving these implanted devices is a considerable drawback of the devices.

There remains a need for an implantable containment apparatus that permits a therapeutic device, such as cell encapsulation device, to be placed and replaced in a patient without or minimally damaging or disturbing tissues associated with the containment apparatus. It is therefore necessary to develop an apparatus that can be easily and atraumatically inserted into host tissue, but that can be easily accessed to remove and replace a therapeutic device.

SUMMARY

The terms "invention," "the invention," "this invention" and "the present invention," as used in this document, are intended to refer broadly to all of the subject matter of this patent application and the claims below. Statements containing these terms should be understood not to limit the subject matter described herein or to limit the meaning or scope of the patent claims below. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

One aspect disclosed herein is an implantable containment apparatus. The containment apparatus is useful for receiving a therapeutic device. The containment apparatus includes a conduit, also referred to as a sheath, that includes an exterior surface and an interior surface, where the interior surface defines a luminal region. The conduit has a first end including a first resealable port and a second end including a second resealable port. The containment apparatus further includes a shaping element, where the shaping element is configured to induce the conduit to have a curved shape. The conduit is adapted to receive a biological moiety or a therapeutic device into the luminal region through the first or the second resealable port.

In some embodiments, a conduit of a containment apparatus disclosed herein includes a laminate of a first layer adjacent to a second layer. Optionally, the first layer includes a first porous material having a first porosity that is impervious to cellular ingrowth across the interior surface of the conduit, and the second layer includes a second porous material having a second porosity that is sufficiently porous to permit growth of vascular tissue from a patient within the pores of the second porous material up to, but not through, the first layer. Optionally, the conduit includes only the second porous material, or includes a laminate of multiple porous materials where each porous material has sufficient porosity to permit growth of vascular tissue from a patient within the pores of the material, such that growth of vascular tissue is permitted through the entire thickness of the material forming the conduit.

In some embodiments, the first and/or second porous material of a containment apparatus disclosed herein is polytetrafluoroethylene (PTFE). In some embodiments, the first and/or the second porous material includes a bioabsorbable material. For example, first and/or the second porous material may include polyglycolide:trimethylene carbonate (PGA:TMC). In some embodiments, the first and/or the second porous material may include both porous PTFE and a bioabsorbable material. For example, the first and/or the second porous material may include a PTFE material coated with a bioabsorbable material or the bioabsorbable material may be incorporated into or onto the first and/or the second porous material in the form of a powder.

In some embodiments, the shaping element includes a shape memory material selected from shape memory alloys and shape memory polymers. In some embodiments, the shaping element is a winding, a strip, a spine, or a stent. In some embodiments, the shaping element is a length of the conduit having an ovoid cross-section. In some embodiments, the shaping element is at least one magnet.

In some embodiments, the containment apparatus further includes at least one fitting for separably joining the first end and the second end. In some embodiments, the at least one, fitting comprises snap fittings, magnetic fittings, weldable fittings, sliding fittings, interference fitting, and/or pressure fittings.

In some embodiments, the containment apparatus further includes one or more sensors. In some embodiments, the one or more sensor is configured to detect temperature, infection, oxygen level, radio-frequency identification (RFID), pressure, pH, glucose, or completion of circuitry.

In some embodiments, disclosed herein is an implantable containment apparatus for a patient in need thereof, the containment apparatus including a conduit including an exterior surface and an interior surface, where the interior surface defines a luminal region having a first end and a second end. The conduit has a first configuration where the ends are unconnected and a second configuration where the ends are connected arid the conduit has a curved shape. The containment apparatus further includes a fitting for removably connecting the first end to the second end.

Another embodiment disclosed herein is a method for implanting a containment apparatus in a tissue bed of a patient that includes inserting, the containment apparatus into a substantially tubular cavity in the tissue bed, where the containment apparatus includes a conduit having an exterior surface, an interior surface defining a luminal region, a first end including a resealable port, and a second end including a resealable port, and a shaping element, where the shaping element is configured to induce the conduit to form a generally toroidal configuration. The conduit is adapted to receive at least one therapeutic device into the luminal region through at least one resealable port. The method further includes placing the apparatus into a generally toroidal configuration.

In some embodiments, placing the apparatus into a generally toroidal configuration includes allowing the apparatus to migrate within the tissue bed into a generally toroidal configuration.

In some embodiments, a method for implanting a containment apparatus in a tissue bed of a patient, further includes deforming the containment apparatus from a primary configuration to a deformed configuration prior to inserting the containment apparatus, where the primary configuration is a generally toroidal configuration.

In some embodiments, a method for implanting a containment apparatus in a tissue bed of a patient further includes joining the first end and the second end.

A further aspect disclosed herein is a method for implanting a containment apparatus in a tissue bed of a patient including inserting a first end of the containment apparatus into a curved, substantially tubular cavity in the tissue bed through an entry point in an incision in the tissue bed, where the containment apparatus includes a conduit including an exterior surface, an interior surface that defines a luminal region, a first end comprising a resealable port, and a second end including a resealable port. The conduit is adapted to receive at least one therapeutic device into the luminal region through at least one resealable port. The method further includes advancing the first end of the containment apparatus in a curved path through the tissue bed, and removing the first end of the containment apparatus through an exit point in the incision in the tissue bed proximate the entry point.

In some embodiments, a method for implanting a containment apparatus in a tissue bed of a patient further includes joining the first end and the second end of the containment apparatus after removing the first end of the containment apparatus.

In some embodiments, a method for implanting a containment apparatus in a tissue bed of a patient further includes placing the apparatus into a generally toroidal configuration.

In some embodiments, a method for implanting a containment apparatus in a tissue bed of a patient further includes deforming the containment apparatus from a primary configuration to a deformed configuration prior to inserting the first end of the containment apparatus into the curved, substantially tubular cavity, where the primary configuration is a generally toroidal configuration.

The apparatus and implantation method disclosed herein reduce trauma to the host tissue as compared to known apparatuses and implantation methods, allowing vascularization in a short period of time so that therapy provided by the biological moiety is immediately available to a patient.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 1A is a top view of an apparatus as described herein having a curved shape where the ends abut according to embodiments disclosed herein.

FIG. 1B is a close up front view of FIG. 1A showing no gap between the ends.

FIG. 2A is a top view of an apparatus as described herein having a curved shape where the ends are separated according to embodiments disclosed herein.

FIG. 2B is a close up front view of FIG. 2A showing a gap between the ends.

FIG. 3 is a top view of an apparatus as described herein having a curved shape where the ends are widely separated according to embodiments disclosed herein.

FIG. 4A is a top view of an apparatus as described herein having a curved shape where the ends are separated and not aligned according to embodiments disclosed herein.

FIG. 4B is a close up front view of FIG. 4A that ends are not aligned.

DETAILED DESCRIPTION

Figure 5:
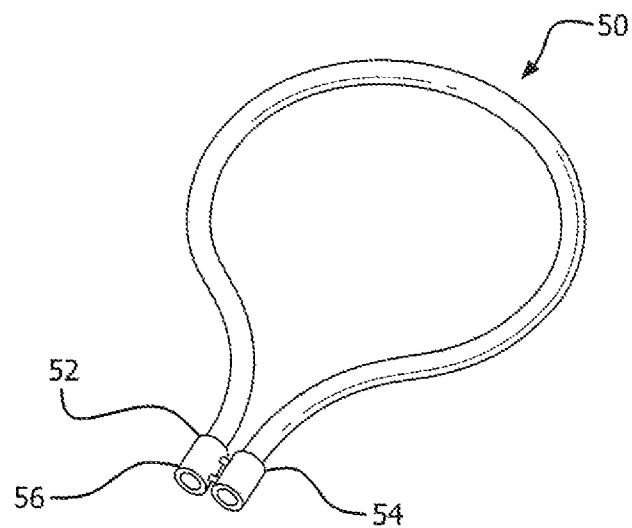
FIG. 5 is a perspective view of an apparatus as described herein having a generally toroidal configuration where the ends are aligned and joined by a removable fitting according to embodiments disclosed herein.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The present invention is directed to an implantable containment apparatus for receiving biological moieties or a therapeutic device, such as a cell encapsulation device, a drug delivery device, or a gene therapy device. Biological moieties suitable for encapsulation and implantation using the devices described herein include cells, viruses, viral vectors, bacteria, proteins, antibodies, and other bioactive moieties. For simplicity, herein the biological moiety is referred to as a cell or cells, but nothing in this description limits the biological moiety to cells or to any particular type of cell, and the following description applies also to biological moieties that are not cells.

The implantable containment apparatus disclosed herein includes a conduit, or tube, with two ends and a shaping element. In some embodiments, the two ends include resealable ports. In some embodiments, the apparatus includes a shaping element. In some embodiments, the apparatus includes one or more fittings to removably join the two ends. Advantageously removably joining the ends allows the implantable containment apparatus to be inserted into a tissue bed and to create a curved shape while being inserted with minimal trauma to the patient. Atraumatic placement allows vascularization to commence immediately or shortly after implantation and allows early, successful insertion of a therapeutic device.

In some embodiments, a containment apparatus may be implanted into a tissue bed, where the containment apparatus is available to house a biological moiety or a therapeutic device containing a biological moiety (such as a plurality of cells). A containment apparatus of embodiments described herein is a curved conduit, or tube, having two ends. The conduit has a luminal region for receiving a therapeutic device. The containment apparatus includes a shaping element, such as a shape memory material or structure made therefrom that induces the apparatus to have a curved shape, such as a generally toroidal configuration, where the two ends may be removably joined together or may rest in close proximity. A containment apparatus disclosed herein reduces trauma to host tissue during implantation and allows a therapeutic device to be inserted without or with only minimal trauma to the patient or to the biological moiety inside the device. Once implanted the apparatus may be accessed to remove an existing therapeutic device and biological moiety and/or to insert a new device and biological moiety.

Apparatus

The implantable containment apparatus disclosed herein includes a conduit, e.g., a sheath, that is configured to receive a therapeutic device (e.g., a cell encapsulation device). In some embodiments, a conduit of an implantable containment apparatus as described herein is a curved tube. In some embodiments, the conduit has a cross-section in a shape that conforms, at least in part, to the form of the therapeutic device the apparatus is intended to contain. As non-limiting examples, the cross-section of the tubular conduit may be circular, ovoid, or elliptical.

In one embodiment, there is provided a shaping element that is configured to induce the conduit to have a curved shape. Curved shape refers to a shape having at least one curve along the length of the conduit and may be continuously curved or curved in different directions and/or planes. In some embodiments, in use the conduit takes on a generally toroidal configuration. Herein, "generally toroidal configuration" means having a looped configuration that can be in one or more planes. When the implantable containment apparatus is in a generally toroidal configuration, the two ends are close in proximity. Thus, a curved shape allows access to both ends of an implantable containment apparatus through one small incision. In some embodiments, however, access to only one end of the implantable containment apparatus is required. In some embodiments, the length of the incision is less than half the diameter of the generally toroidal configuration of the device. Also, the curved shape allows easy insertion and removal of a biological moiety or a therapeutic device into/out of the implantable containment apparatus.

Some non-limiting examples of generally toroidal configurations are shown in FIGS. 1-5. An apparatus having a closed loop is shown in FIG. 1. FIG. 1, panel A is a top view of an apparatus 10 as described herein having a generally toroidal configuration where the first end 12 faces and abuts the second end 14. FIG. 1, panel B is a partial front view of the abutting ends 12, 14 of the apparatus as viewed in the direction of the arrow in panel A. In some embodiments, in use, the ends may abut but may be separated temporarily to access the interior of the apparatus. In some embodiments, the surfaces of the facing ends lie in parallel planes as shown in FIG. 2. FIG. 2, panel A is a top view of an apparatus 20 as described herein having a generally toroidal configuration where the first end 22 faces but does not abut the second end 24. FIG. 2, panel B is a partial front view of the ends 22, 24 of the apparatus as viewed in the direction of the arrow in panel A. In some embodiments the surface of the facing ends do not lie in parallel planes as shown in FIG. 3. FIG. 3, panel A is a top view of an apparatus 30 as described herein having a generally toroidal configuration where the first end 32 faces but does not abut the second end 34, and where the facing ends do not lie in parallel planes. FIG. 4 panel A is a top view of an apparatus 40 as described herein having a generally toroidal configuration wherein the apparatus 40 is slightly helical such that the first end 42 and second end 44 face opposite directions but do not face each other. FIG. 4, panel B is a partial front view of the ends 42, 44 of the apparatus as viewed in the direction of the arrow in panel A. In this configuration, the ends are in close proximity, but do not block access to each other. FIG. 5 is a perspective view of an apparatus 50 as described herein in a generally toroidal configuration where the ends 52, 54 are aligned and joined by a fitting 56 parallel to each other.

Figure 6:
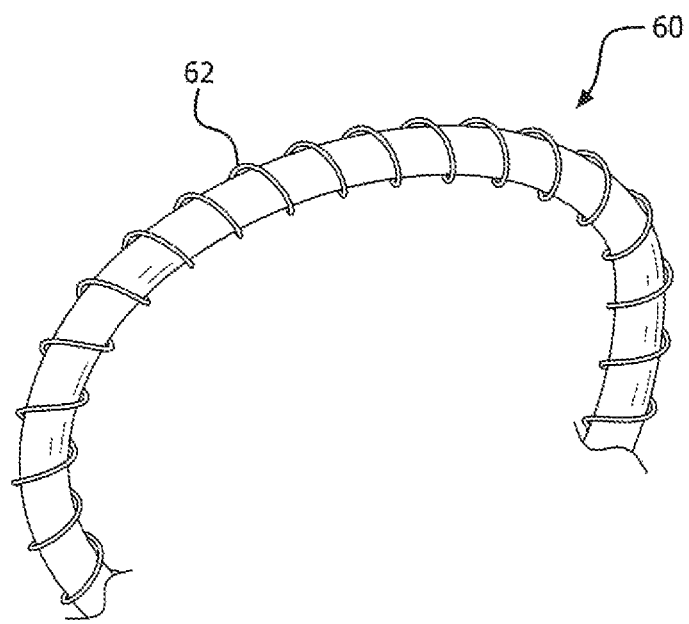
FIG. 6 is a partial view of an apparatus as described herein having a shaping element in form of a wrapping according to embodiments disclosed herein.
Figure 7:
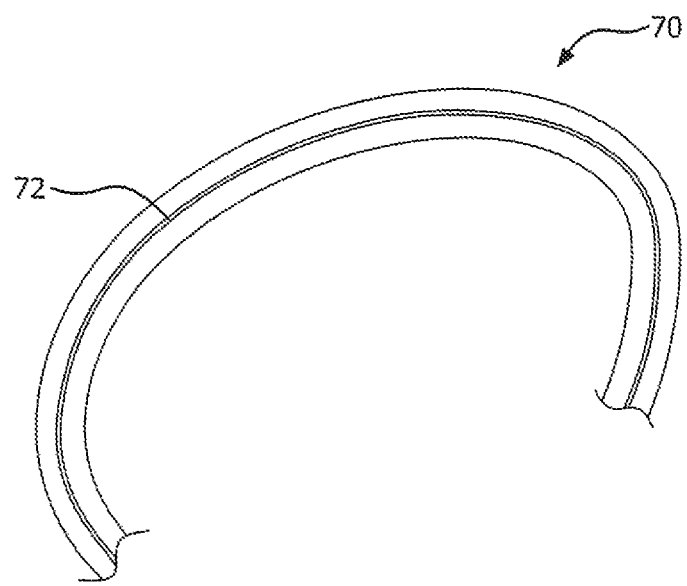
FIG. 7 is a partial view of an apparatus as described herein having a shaping element along an exterior surface of the apparatus according to embodiments disclosed herein.
Figure 8:
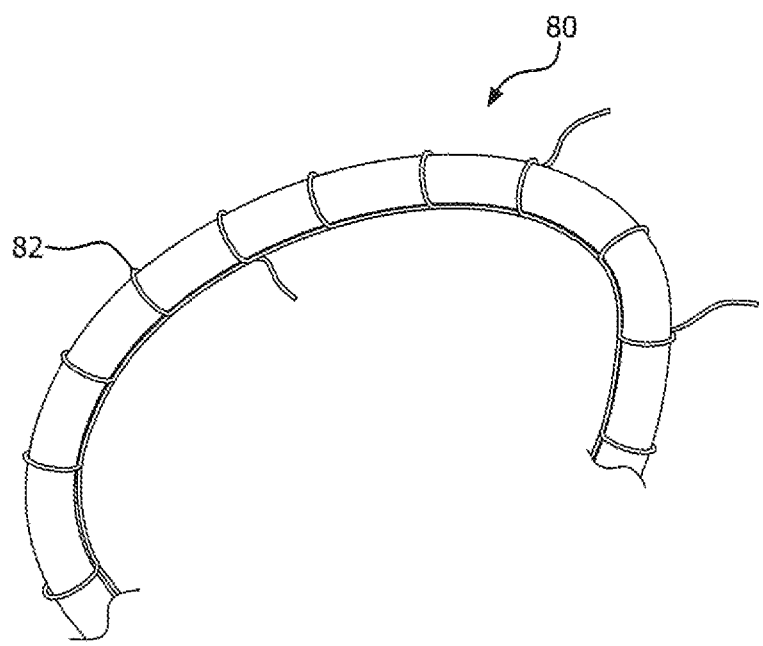
FIG. 8 is a partial view of an apparatus as described herein having a shaping element along an exterior surface of the apparatus according to embodiments disclosed herein.

In some embodiments, the apparatus includes a shaping element. The shaping element induces the conduit into a primary, curved shape, such as a generally toroidal configuration, in a tissue bed. In some embodiments, the shaping element may also hold the apparatus in that primary shape during implantation and subsequent use. Non-limiting examples of useful shaping elements include windings, strips, spines, stents, and combinations thereof. As non-limiting examples, the shaping elements may be on the exterior surface of the conduit, between the layers of the conduit, or along the interior surface of the conduit. Some non-limiting examples of shaping elements are shown in FIGS. 6-9. FIG. 6 is a partial top view of an apparatus 60 as described herein that includes a winding 62. FIG. 7 is a partial top view of an apparatus 70 as described herein including a spine 72. FIG. 8 is a partial top view of an apparatus 80 as described herein including a combination of a plurality of rings 82 and a spine 84. A shaping element provides several advantages. In one embodiment, the shaping element provides the ability to insert a containment apparatus in any configuration convenient for insertion, and once inserted, the device independently assumes a primary in-use configuration. In one embodiment, the shaping element holds a containment apparatus in a primary configuration in use such that the biological moiety or therapeutic device(s) can easily be removed from and inserted into the apparatus. In some embodiments, the shaping element adopts its primary configuration at a temperature consistent with physiological temperature, e.g. about 37° C.

In some embodiments, the shaping element includes a shape memory material or structure made therefrom. Non-limiting examples of useful shape memory materials include shape memory alloys, such as nitinol, and shape memory polymers such as polyetheretherketone, polymethyl methacrylate, polyethyl methacrylate, polyacrylate, poly-alpha-hydroxy acids, polycapropactones, polydioxanones, polyesters, polyglycolic acid, polyglycols, polylactides, polyorthoesters, polyphosphates, polyoxaesters, polyphosphoesters, polyphosphonates, polysaccharides, polytyrosine carbonates, polyurethanes, and copolymers or polymer blends thereof. In addition to inducing the conduit into a primary configuration in use, the shape memory element facilitates implantation, including facilitating any change in profile of the apparatus during implantation.

In some embodiments, the apparatus does not include a shape memory material, but the geometry of the apparatus, e.g. the radial cross-section of the conduit, forces the apparatus into a generally toroidal conformation. In those embodiments, the geometry is the shaping element. In some embodiments, a flexible apparatus may take on a curved shape, such as a generally toroidal configuration, when the ends are joined, even without a shaping element.

In some embodiments, the conduit of the containment apparatus as described herein is made, primarily, of a porous polymeric material having selective sieving properties. The shaping element does not interfere with the porosity of the apparatus. A selectively sieving porous polymeric material controls passage of solutes, biochemical substances, viruses, and cells, for example, through the material, primarily on the basis of size. In general, as the average pore size of a porous polymeric material increases, increasingly larger biochemicals and biological entities are able to pass through the material.

Polymers having suitable selective permeability and/or porous properties and which may be useful for construction of an apparatus as described herein include, but are not limited to, alginate, cellulose acetate, polyalkylene glycols such as polyethylene glycol and polypropylene glycol, pan-vinyl polymers such as polyvinyl alcohol, chitosan, polyacrylates such as polyhydroxyethylmethacrylate, agarose, hydrolyzed polyacrylonitrile, polyacrylonitrile copolymers, polyvinyl acrylates such as polyethylene-co-acrylic acid, porous polytetrafluoroethylene (PTFE), modified PTFE polymers, tetrafluaroethylene ethylene (TFE) copolymers, porous polyalkylenes such as porous polypropylene and porous polyethylene, porous polyvinylidene fluoride, porous polyester sulfone, porous polyurethanes, porous polyesters, and copolymers and combinations thereof, as well as woven or non-woven collections of fibers or yarns, or fibrous matrices, either alone or in combination. In some embodiments, the porous polymeric materials is expanded PTFE membrane that may be characterized as a porous material having void spaces defined by nodes and fibrils.

Figure 9:
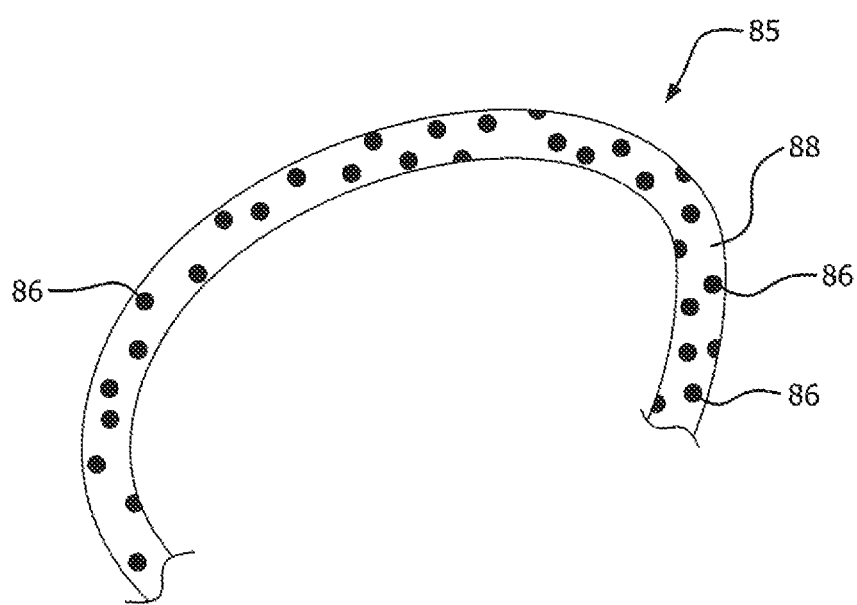
FIG. 9 is a partial view of an apparatus as described herein having a bioabsorbable material distributed on the exterior surface of the apparatus according to embodiments disclosed herein.

In some embodiments, the porous polymeric material may be a bioabsorbable material. Alternatively, a porous polymeric material may be coated with a bioabsorbable material or a bioabsorbable material may be incorporated into or onto the porous polymeric material in the form of a powder. Coated materials may promote infection site reduction, promoting vascularization and favorable type 1 collagen deposition. The porous materials described herein may include any bioabsorbable material known in the art. Non-limiting examples include, but are not limited to, polyglycolide:trimethylene carbonate (PGA:TMC), polyalphahydroxy acid such as polylactic acid, polyglycolic acid poly (glycolide), and poly(lactide-co-caprolactone), poly(caprolactone) poly(carbonates), poly(dioxanone), poly (hydroxybutyrates), poly(hydroxyvalerates), poly (hydroxybutyrates-co-valerates), and copolymers and blends thereof. FIG. 9 shows an apparatus 85 as described herein including a distributed amount of a bioabsorbable material 86 interspersed as a powder on the surface 88 of the apparatus 85.

The bioabsorbable material may be formed as a solid (molded, extruded, or crystals), a self-cohered web, or a raised webbing. In some embodiments, one or more layers of bioabsorbable material are attached to a non-bioabsorbable material having macroscopic porosity to allow for cell permeation to form a composite. In other embodiments, a non-bloabsorbable having microscopic porosity to decrease or prevent cell permeation is releasably attached to the porous self-cohered web to permit atraumatic removal of the containment tube from the body of a patient days following implantation. Resorbing into the body can promote favorable type 1 collagen deposition, neovascularization, and a reduction of infection.

Figure 10:
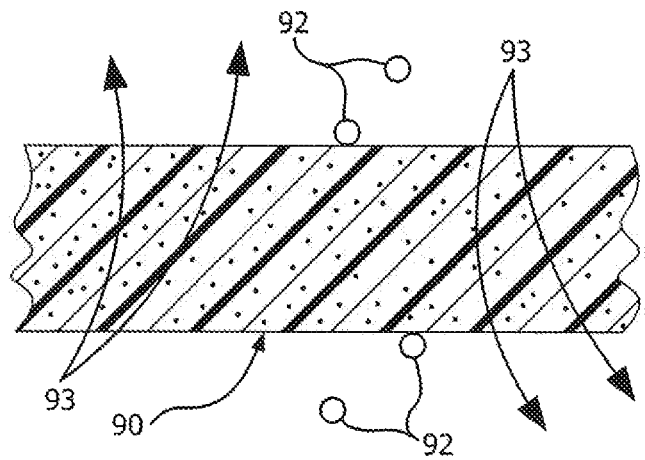
FIG. 10 is a cross-sectional view of a porous polymeric material for the first layer of the conduit as described herein.

In some embodiments, where a material is porous only through a portion of its thickness, the molecular weight cutoff, or sieving property, of a selectively permeable, porous, polymeric material (e.g., an ePTFE membrane) begins at the surfaces of the material. As a result, certain solutes and/or cells do not enter and pass through the porous spaces of the material from one side to the other. FIG. 10 is a cross-sectional view of a porous polymeric material 90 useful in some embodiments of a conduit described herein, where the selective permeability of the material 90 excludes cells 92 from migrating or growing into the porous spaces of material while permitting bi-directional flux of solutes 93 across the thickness of the material. Vascular endothelial cells can combine to form capillaries thereon. Such capillary formation or neovascularization of the conduit of the containment apparatus permits fluid and solute flux between tissues of a patient and the contents of a therapeutic device to be enhanced.

Figure 11:
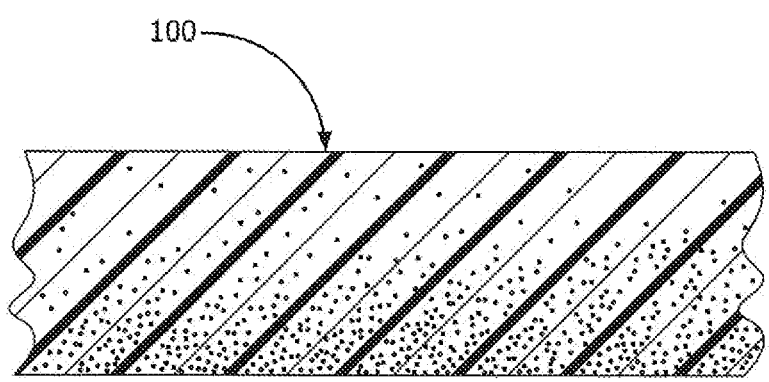
FIG. 11 is a cross-sectional view of a porous polymeric material having gradient porosity for use in a conduit as described herein.
Figure 12:
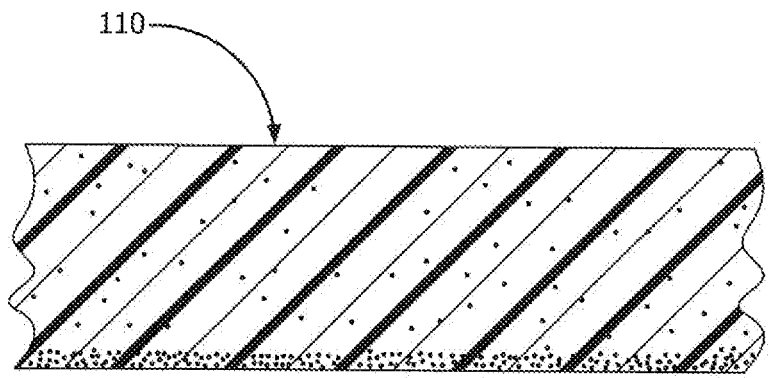
FIG. 12 is a cross-sectional view of a porous polymeric material having gradient porosity for use in a conduit as described herein.

In some embodiments, permeability of a porous polymeric material can be varied continuously across the thickness of the material. FIG. 11 is a cross-sectional view of a porous polymeric material 100 useful in a conduit described herein, where the selective permeability of the material 100 varies continuously across the thickness of the material as indicated by the gradually increasing density of the stippling in the figure. FIG. 12 is a cross-sectional view of a porous polymeric material of the present invention 110 useful in a conduit described herein, where the selective permeability of the material 110 varies across the thickness of the material as indicated by the increasing density of the stippling in the figure.

Figure 13:
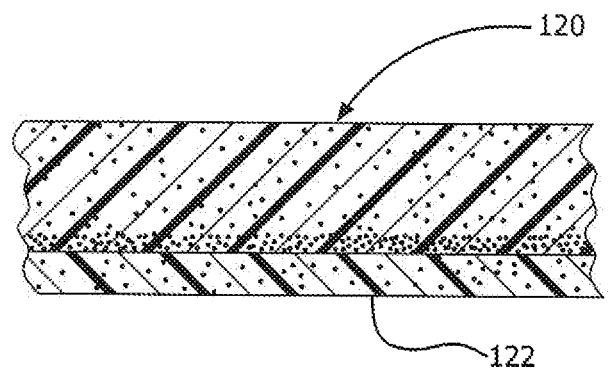
FIG. 13 is a cross-sectional view of a porous polymeric material having a first and second layer for use in a conduit as described herein.

In one embodiment the permeability of the porous polymeric material is varied across its thickness with additional layers of porous polymeric material. FIG. 13 is a cross-sectional view of a porous polymeric material 120 useful in a conduit described herein, where the selective permeability of the material is varied across the thickness of the material 120 with an additional layer of porous polymeric material 122. The additional layers of porous polymeric material may have the same composition and permeability as the initial layer of material or the additional layers may be of a different composition and/or permeability.

Figure 14:
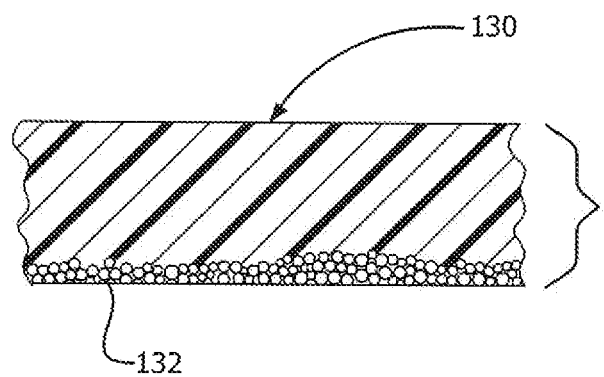
FIG. 14 is a cross-sectional view of a porous polymeric material including a hydrogel for use in a conduit as described herein.

In another embodiment, the selective permeability of a porous polymeric material is varied by impregnating the void spaces of the porous polymeric material with a hydrogel material. A hydrogel material can be impregnated in all or substantially all of the void spaces of a porous polymeric material or in only a portion of the void spaces. For example, by impregnating a porous polymeric material with a hydrogel material in a continuous band within the material adjacent to and/or along the interior surface of a porous polymeric material, the selective permeability of the material is varied from an outer cross-sectional area of the material to an inner cross-sectional area of the material. FIG. 14 is a cross-sectional view of a porous polymeric material 130 useful in a conduit described herein, where the selective permeability of the material 130 is varied across the thickness 132 of the material with a hydrogel material 133.

The amount and composition of hydrogel material impregnated in a porous polymeric material depends in large part on the particular porous polymeric material used to construct an apparatus of the present invention, the degree of permeability required for a given application, and the biocompatibility of the hydrogel material. Non-limiting examples of hydrogel materials include, but are not limited to, hydrolyzed polyacrylonitrile, alginate, agarose, carrageenan, collagen, gelatin, polyvinyl alcohol, poly(2-hydroxyethyl methacrylate), poly(N-vinyl-2-pyrrolidone), polyethylene glycol, polyethyleneimine, fibrin-thrombin gels, or gellan gum, and copolymers thereof, either alone or in combination. In some embodiments, the total thickness of a porous PTFE/hydrogel composite may range from about 2 microns to about 1000 microns.

Figure 15:
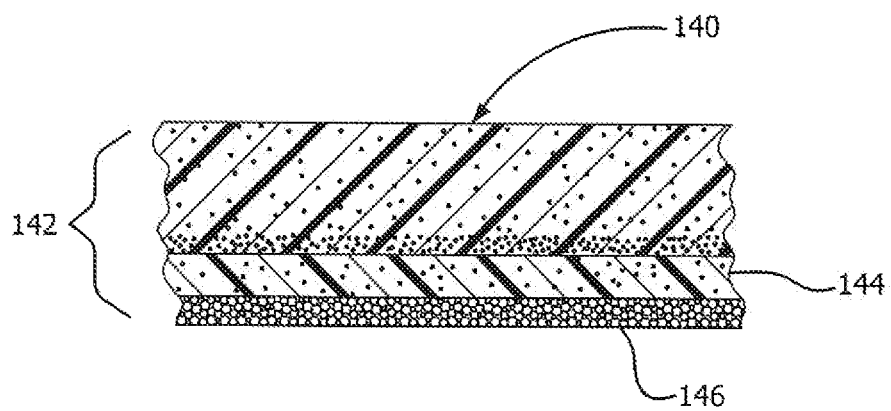
FIG. 15 is a cross-sectional view of a porous polymeric material a first and second layer and a hydrogel for use in a conduit as described herein.

In some embodiments, the permeability of the porous polymeric material may be varied across the thickness of the material with an additional layer of porous polymeric material and a further layer of hydrogel material. FIG. 15 is a cross-sectional view of a porous polymeric material 140 useful in a conduit described herein, where the selective permeability of the material 140 is varied across the thickness 142 of the material with an additional layer of porous polymeric material 144 and a further layer of hydrogel material 146. An advantage of this embodiment is the additional protection provided an implant patient against contamination with cells from a failed therapeutic device contained in an apparatus as described herein. In addition, this configuration will provide a strong cell and humoral immunoisolation barrier.

Figure 16:
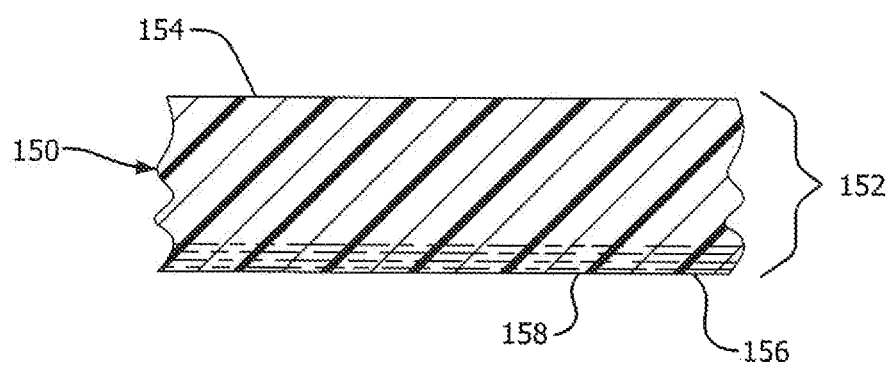
FIG. 16 is a cross-sectional view of a porous polymeric material and a cell exclusion zone of a conduit as described herein.

In some embodiments, the permeability of the porous polymeric material is selected to permit growth of cells from a patient into, but not through, the material. In some embodiments, a cell permeable zone is formed in the void spaces of a porous polymeric material starting at the exterior surface of the material and continuing to a point within the material adjacent to the interior surface of the apparatus where the permeability of the porous polymeric material to cells is decreased so that cells that have migrated into the void spaces of the material cannot migrate further and penetrate the interior surface of the apparatus. FIG. 16 is a cross-sectional view of a porous polymeric material 150 useful in a conduit described herein, having a cell permeable zone 152 beginning at the exterior surface 154 of the material 150 and continuing across the thickness of the material 150 to a cell exclusion zone 156 within the material 150 adjacent to and continuous with the interior surface 158 of the material.

The region of the porous polymeric material in which cells cannot migrate or grow is referred to as a cell exclusion zone and the cell exclusion zone is referred to herein as impervious to cellular ingrowth. A cell exclusion zone prevents or minimizes invasive cells from entering the lumen of the apparatus and contacting, adhering to, fouling, ingrowing, overgrowing, or otherwise interfering with a therapeutic device contained within the apparatus. To exclude invading host cells from growing through to the interior surface of the apparatus, in some embodiments, the pore size of the cell exclusion zone may be less than about 5 microns, less than about 1 micron, or less than about 0.5 microns, as measured by porometry.

In some embodiments the permeability may be adjusted with a hydrogel material. For example, in some embodiments, a cell exclusion zone can be formed in an expanded PTFE membrane having a cell permeable zone by impregnating the void spaces of the expanded PTFE membrane with a hydrogel material in a continuous band within the expanded PTFE membrane adjacent to and/or along the interior surface of the expanded PTFE membrane of an apparatus. The hydrogel material forming the cell exclusion zone may have a thickness from about 2 µm to about 100 µm or from about 25 µm and about 50 µm.

Various cell types can grow into the cell permeable zone of a porous polymeric material of an apparatus as described herein. The predominant cell type that grows into a particular porous polymeric material depends primarily on the implantation site, the composition and permeability of the material, and any biological factors, such as cytokines and/or cell adhesion molecules, for example, that may be incorporated in the material or introduced through the apparatus. In some embodiments, vascular endothelium is the predominant cell type that grows into a porous polymeric material for use in the present invention. Vascularization of the porous polymeric material by a well-established population of vascular endothelial cells in the form of a capillary network is encouraged to occur as a result of neovascularization of the material from tissues of a patient into and across the thickness of the material very close to the interior surface of the apparatus, but not across the cell exclusion zone.

Figure 17:
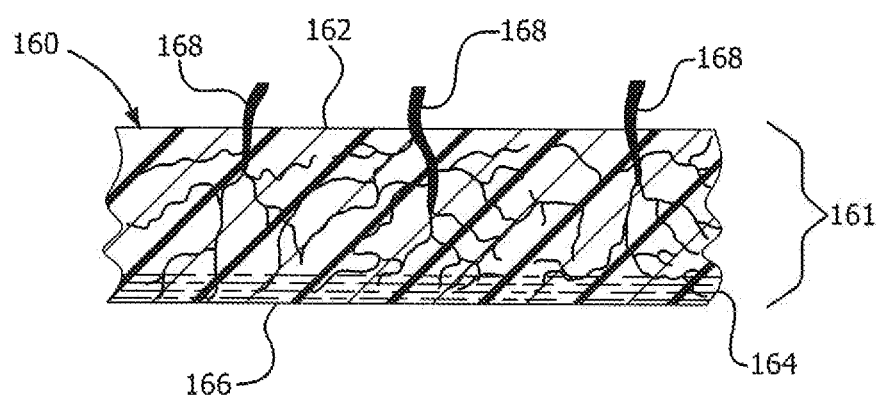
FIG. 17 is a cross-sectional view of a conduit showing ingrowth a vascular tissue as described herein.

FIG. 17 is a cross-sectional view of a porous polymeric material 160 useful in a conduit described herein, having a cell permeable zone 161 beginning at the exterior surface 162 of the material 160 and continuing across the thickness of the material 160 to a cell exclusion zone 164 within the material 160 adjacent to and continuous with the interior surface 166 of the material, wherein the cell permeable zone 161 is populated with vascular structures 168. Neovascularization of an apparatus improves mass transport of therapeutic drugs or biochemical substances between the interior surface of conduit and tissues of a patient, thereby enhancing the quantity and rate of transport of therapeutic drugs or biochemical substances between the contents of a therapeutic device housed in the containment tube and tissues of the patient.

In some embodiments, maximum exchange of materials between a therapeutic device and tissues of a patient is achieved when the maximum distance from the ingrown capillaries to the lumen of the conduit is less than about 250 microns. In some embodiments, the maximum distance from the ingrown capillaries to the lumen of the conduit is less than about 100 microns, less than about 50 microns, or less than about 25 microns. Accordingly, in some embodiments, the cell exclusion zone may be less than about 250 microns, less than about 100 microns, less than about 50 microns, or less than about 25 microns, in thickness. In addition to permitting vascularization of the porous polymeric material, the permeability of the porous polymeric material may be chosen to selectively permit passage of biochemical substances, including therapeutic drugs, having molecular weights up to about 5,000,000 MW across the thickness of the material.

In some embodiments an apparatus is inserted in a configuration similar to or dissimilar to its final configuration, but for the apparatus to assume its final shape, some migration of the implanted apparatus may occur. Vascularization and other tissue ingrowth of the cell permeable zone of a containment apparatus as described herein can anchor the apparatus in the implantation site. This anchoring however does not prevent migration of the apparatus into its primary shape because that shape migration occurs shortly after implantation before significant vascularization and other tissue growth occurs, and is a result of significant forces exerted by the shape memory element or by the fittings joining the ends of the apparatus. The anchoring minimizes or prevents the apparatus from moving from the implantation site over time and once sufficient anchoring has occurred, can assist the apparatus in maintaining its shape. Maintaining the shape of a tubular apparatus as described herein is often necessary for easy placement, replacement, and proper functioning of a therapeutic device contained in the apparatus.

A containment apparatus as described herein has one or more resealable ports through which a biological moiety or a therapeutic device may be placed, retrieved, and replaced in the apparatus. In some embodiments, the resealable port is secured through the porous polymeric material of an apparatus as described herein or secured in an open end of a tubular, or similarly shaped, apparatus configuration. A resealable port can have any shape suitable for facilitating placement, retrieval, and replacement of a therapeutic device in the luminal region of a particular apparatus embodiment. In some embodiments, commercially available fittings, such as Luer-lok connectors, are useful as an resealable ports in the containment apparatus described herein. In some embodiments, the resealable port is a hollow cylindrically shaped fitting made of PTFE having a first portion that fits snugly inside an end of the tube component of an apparatus described herein and a second portion that extends beyond the end of the tube component to receive and retain a sealing element. In some embodiments, the resealable port can be fabricated by injection molding of a fitting onto the end of a tubular apparatus using techniques known to those skilled in the art as insert molding. In some embodiments, the resealable port is a hole in a porous polymeric material with one or more flexible pieces, or flaps, of porous polymeric material positioned to cover and close the hole. The flaps may be formed as part of the apparatus or may be attached to the apparatus subsequent to its initial construction.

In some embodiments, a resealable port may be repeatedly opened and closed with a seal. Useful seals include, but, are not limited to, caps, plugs, clamps, compression rings, or valves. The seal may be attached to the resealable port with friction, by clamping, or with a screw comprised of threads and grooves. Depending on the intended use of the apparatus, the resealable port is sealed to create a hermetical seal, a fluid-tight seal, or a non-fluid-tight seal. In some embodiments, an apparatus intended for permanent or long term (i.e. at least about three weeks) implantation in a patient, may be sealed with a hermetical or a fluid-tight seal.

Many of the materials used to construct an apparatus as described herein are inherently radio-opaque. Those materials that are not inherently radio-opaque can be modified to be radio-opaque by impregnation of the material with barium, for example. Other useful methods for rendering a material radio-opaque are known to those skilled in the art. The radio-opacity of materials used to construct an apparatus as described herein is mainly used to facilitate surgical placement of the apparatus or to locate the apparatus in a patient following implantation.

In some embodiments, a containment apparatus as described herein is in the form of an implantable conduit for containing a biological moiety or a generally cylindrically shaped therapeutic device. In some embodiments, the implantable tube may be made of an expanded PTFE membrane having a cell permeable zone extending from the exterior surface of the conduit through to a cell exclusion zone radially inward from the cell permeable zone, where the cell exclusion zone terminates at the luminal surface of the tube. The cell permeable zone is sufficiently porous for capillaries to form therein. In some tubular embodiments of the apparatus, open ends of the tube can be prevented from collapsing with a stent, or core. The stent can be in any shape and made of any biocompatible material useful for keeping all or part of a tubular apparatus in an opened, or expanded, tubular form during storage and/or following implantation. Useful materials for a stent include, but are not limited to, stainless steel, titanium, and hydrogels. To maintain the entire length of a tubular apparatus in an expanded configuration when a therapeutic device is not inserted, an inert core simulating the shape and resilience of a therapeutic device may be placed in the apparatus. Suitable core materials include, but are not limited to, polytetrafluoroethylene, expanded polytetrafluoroethylene, polydimethysiloxane, polyurethane, polyester, polyimide, or hydrogels derived from polysaccharides, alginate, hydrolyzed polyacrylonitrile, and combinations thereof.

In some embodiments, the material for the conduit of the containment apparatus is a laminate of at least two materials having different porosities. In some embodiments, the material has at least two layers of an expanded PTFE membrane, each membrane having different porosities. In some embodiments, the portion of the laminate containing the cell exclusion zone may have an average pore size ranging between about 0.05 microns and about 0.4 microns, as measured by porometry. In some embodiments the pore size of this material may be about 0.4 microns. In some embodiments, the thickness of the material may be between about 1 micron and about 25 microns.

In some embodiments, the material used as the cell permeable zone has an average pore size greater than about 3.0 microns, or greater than about 5.0 microns, as measured by fibril length. In some embodiments, the thickness of the material ranges from about 10 microns to about 1000 microns, or from about 40 microns to about 60 microns.

In one embodiment, the tube has resealable port at both ends of the tube, and a therapeutic device may be moved in and out of the luminal region of the tube through either port.

Figure 18:
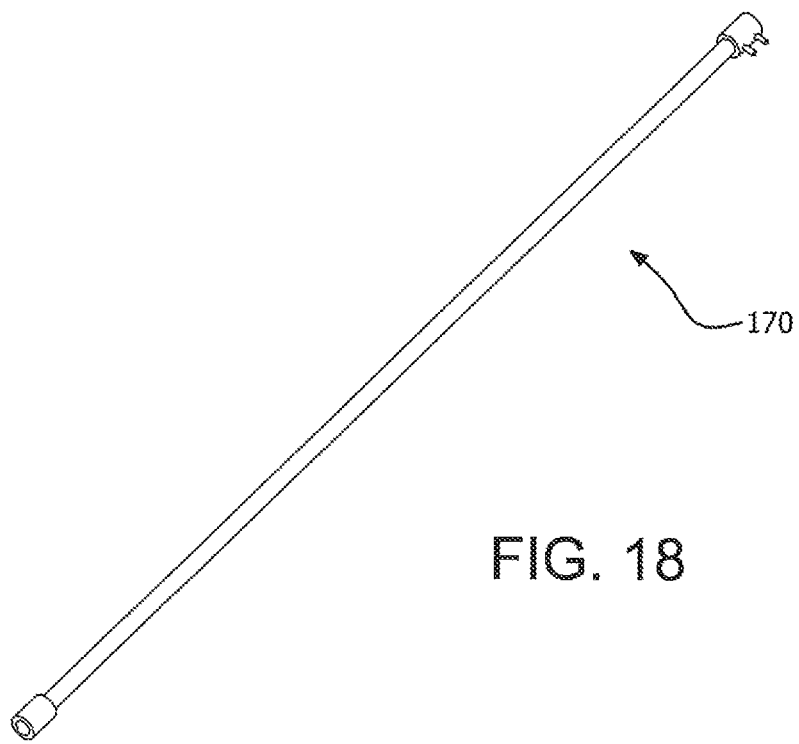
FIG. 18 is a partial view of a device as described herein including one example a snap fitting joining two ends according to embodiments disclosed herein.

FIG. 18 is a perspective view of an implantable apparatus as described herein. FIG. 18 shows the apparatus 170 deformed from its original curved configuration into a generally straight configuration. An apparatus described herein may be deformed into configurations other than toroidal (for example, less curved, linear, or generally linear) to facilitate insertion into a tissue bed.

The size of the apparatus will vary depending on the size of the therapeutic device to be inserted. Multiple apparatuses may be implanted in a single individual, resulting in multiple conduits being implanted into the individual. Alternatively, the apparatus may include more than one conduit.

Fittings

In some embodiments, the apparatus also includes one or more fittings for separably joining the two ends.

"Join", "joined" and "joining" are defined herein as connected either with contact, such as abutting, or by being held in close physical proximity as by a fitting that contacts each end, but where the ends do not necessarily abut each other. "Separable" and "separably" are defined herein as able to be brought together in a fixed configuration and subsequently re-separated.

In some embodiments, the ends of the apparatus are separably joinable by at least one fitting. In some embodiments, each of the ends of the apparatus may contain a fitting, or a portion of a fitting, or one end may contain the fitting. Advantageously the fittings separably join the ends to achieve and/or maintain a curved configuration. A variety of fittings are known to persons skilled in the art and may be employed. For example, snap fittings, magnetic fittings, weldable fittings, sliding fittings, interference fitting, or pressure fittings, are all acceptable fittings.

Figure 19:
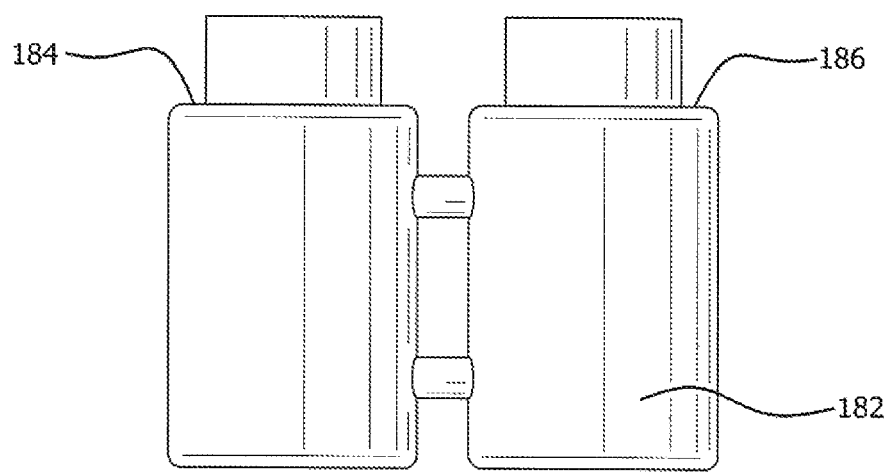
FIG. 19 is a partial view of an apparatus as described herein including a fitting covering and joining a first end and a second end.

FIG. 19 is a partial view of an apparatus as described herein including a fitting 182 covering and joining a first end 184 and a second end 186 of an apparatus as described herein.

Figure 20:
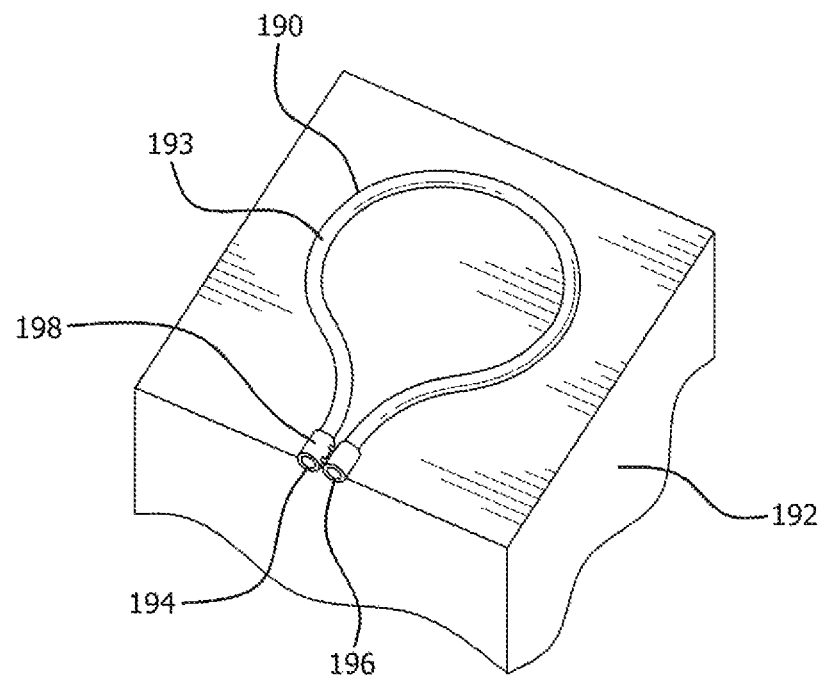
FIG. 20 is a perspective view of an implantable device disposed in a tissue bed according to embodiments disclosed herein.

FIG. 20 is a top view of an implantable apparatus 190 according to embodiments disclosed herein disposed in a tissue bed 192. The apparatus 190 has an outer sheath 193 and first and second ends 194, 196, which are joined by a fitting 198 giving the apparatus 190 a generally toroidal shape.

Sensors

Figure 21:
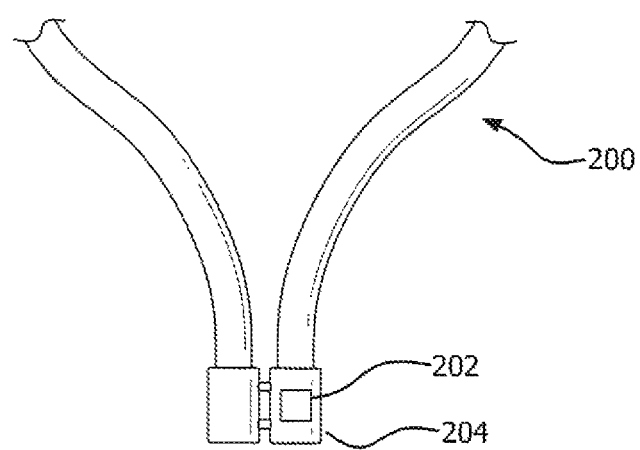
FIG. 21 is a partial view of an implantable device including a sensor according to embodiments disclosed herein.

Optionally, the apparatus may include one or more sensors. These sensors could be contained in the apparatus, for example in one or more of the conduit, the ends, or the resealable port. FIG. 21 is a partial top view of an apparatus 200 as described herein including a sensor 202 on one end 204. In some embodiments, a sensor can be configured to detect temperature, infection, oxygen levels, pressure, pH, or glucose levels. In some embodiments, the sensor is radio opaque. In some embodiments, the sensor enables a clinician to locate the ends of the containment apparatus in the tissue bed, for example, for removal or replacement of a therapeutic device within the containment apparatus. The sensors can optionally contain radio frequency identification (RFID) technology. In some embodiments, one or more of the sensors includes one or more magnets. In some embodiments, a magnet or magnets can be used to aid in the positioning of the therapeutic delivery device. In some embodiments, a sensor completes a circuit, allowing the device to signal it is in its final configuration and activating various sensors.

Methods

Also provided herein are methods for implanting an implantable containment apparatus for housing a therapeutic device. The apparatus is implanted into a patient by creating a tissue tract in the patient and inserting the apparatus into the tract.

In some embodiments, a method for implanting an implantable containment apparatus in a patient includes creating a curved, substantially-tubular tract (e.g. opening or cavity) in a tissue bed and inserting the implantable containment apparatus into the tract. In some embodiments, the tissue tract is an arced, substantially-tubular tract. An arced tract is curved with no inflection point. As used herein, arced does not necessarily indicate a constant radius. In some embodiments, however, the arced tract may have a generally constant radius. In some embodiments, the arced tract lies in a single plane.

The insertion of the implantable containment apparatus can take place during the formation of the tissue tract or subsequent to the formation of the tissue tract. In some embodiments, during insertion, the apparatus enters the tissue through an incision at an entry point and exits the tissue through the same incision at an exit point near the entry point. In some embodiments, once inserted, the two ends of the apparatus are in close proximity. In some embodiments, the two ends of the apparatus are joined. In some embodiments, the ends of the apparatus are joined with the ends facing toward each other. In some embodiments, immediately after insertion the two ends of the apparatus are not in close proximity (for example, the device may be in a linear configuration), but after insertion the device migrates in viva into a configuration where the two ends of the apparatus are in close proximity.

Insertion

In some embodiments, the generally toroidal configuration of the apparatus is a primary, configuration, which is its configuration in use, and the apparatus also has a deformed configuration that is straighter or generally linear. In some embodiments, the apparatus is deformed from a primary generally toroidal configuration to a generally linear configuration prior to implantation, and after implantation the shaping element facilitates the return of the apparatus to its primary shape. In some embodiments, the apparatus assumes its primary configuration at a temperature that is approximately body temperature, e.g. 37° C.

In some embodiments, with creation of the cavity and either simultaneous insertion of the implantable containment apparatus or later insertion of the apparatus, a first end of the apparatus is inserted through an incision into a tissue bed and the apparatus is moved through the tissue bed in a curved path. The first end of the apparatus exits from the same incision proximate the entry point such that the first and second ends of the apparatus can be accessed simultaneously. FIGS. 22A-22F show several stages of insertion. Tools for holding and advancing the implantable containment apparatus through the tissue bed are not shown and are not limited as long as the apparatus traverses the entirety of the tract and protrudes from the tract in close proximity to the entry point. As non-limiting examples, tools for inserting and advancing an apparatus as described herein include a tunneling tool that is simultaneously creating the cavity in the tissue bed, a placement tool that places the apparatus into an existing tract in the tissue and then is removed from the tissue leaving the apparatus, an injection tool (e.g. a syringe or similar device) that remains outside the tissue tract or extends a limited distance into the tissue tract and forces the apparatus into the tract using a plunger or similar device, and/or a grasping tool that holds a portion of the apparatus while inserting and steering it through the tissue tract.

Figure 22A:
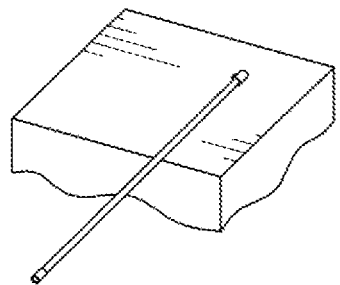
FIG. 22A-FIG. 22F are a stepwise illustration of one embodiment of an insertion step according to methods described herein.
Figure 22B:
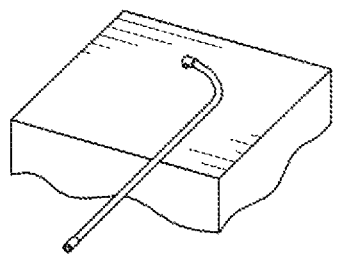
Figure 22C:
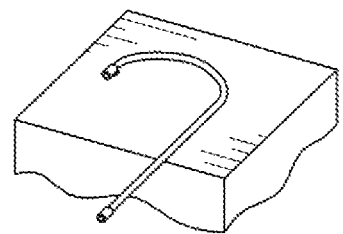
Figure 22D:
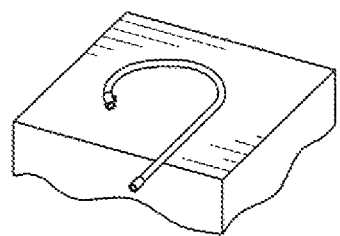
Figure 22E:
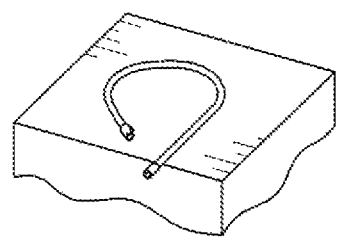
Figure 22F:
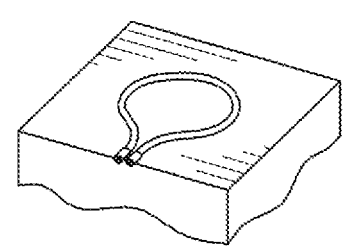

In some embodiments an implantable containment apparatus is inserted in a configuration similar or dissimilar to its final configuration, and for the apparatus to assume its final shape, some migration of at least a portion of the implanted apparatus may occur. FIGS. 22E and 22F show migration of an apparatus as described herein after insertion into a tissue bed.

Optionally, the implantable containment apparatus is made partially or entirely of a shape memory element to facilitate insertion, including any change in profile. Optionally, the apparatus includes an ovoid cross-section to ensure preferential bending and preventing kinking when transitioning form a linear profile to a toroidal profile.

In some embodiments, upon a shape transition, the microstructure of the outer sheath layer can change. Such a change can delay or enable vascularization and/or tailor the bioactive release profile of the apparatus. This can help minimize trauma to the tissues, minimize necrosis of the contained cells, and/or delay a patient's immune response to the apparatus.

Insertion Timing

In some embodiments, the inserting step may be carried out simultaneously with the step of creating a curved, substantially-tubular cavity in the tissue bed. For example, a hollow tunneling tool may be used to create the curved, substantially-tubular cavity in the tissue bed, and the implantable containment apparatus may be inside the hollow tunneling tool while the tissue cavity is created such that the tunneling tool may be removed while the implantable containment apparatus remains in the tissue.

Optionally, the inserting step may be carried out a period of time after the step of creating the cavity in the tissue bed. For example, the apparatus may be inserted immediately or a short period of time (e.g., 5 minutes or less, 30 minutes or less, 1 hour or less, or one day or less) after creating the cavity in the tissue bed, optionally as part of a single procedure. Alternatively, the apparatus may be inserted a longer period of time (e.g., 1 day or more, 1 week or more, or one month or more) after creating the cavity in the tissue bed as part of a separate procedure.

Joining

In some embodiments, the method further includes joining the first and second ends of the implantable containment apparatus. In some embodiments, joining the ends facilitates forming or maintaining a generally toroidal configuration. In some embodiments, joining includes the step of using a fitting to hold the first and second ends in close proximity. In some embodiments joining includes using a fitting tool to hold the first and second ends in a configuration where the ends face each other. In some embodiments joining is a consequence of two ends of the apparatus migrating into close proximity or until they abut because fittings on each of the two ends of the device have a natural affinity for each other, e.g., magnetic fittings. For example, in some embodiments, an apparatus as described herein and having magnetic fittings on the first and second ends may be have a non-toroidal configuration immediately after implantation, e.g. a linear or non-linear, non-toroidal configuration. The magnetic fittings are attracted to each other and induce migration until the two magnetic ends are in close proximity, forming a generally toroidal configuration.

Figure 23:
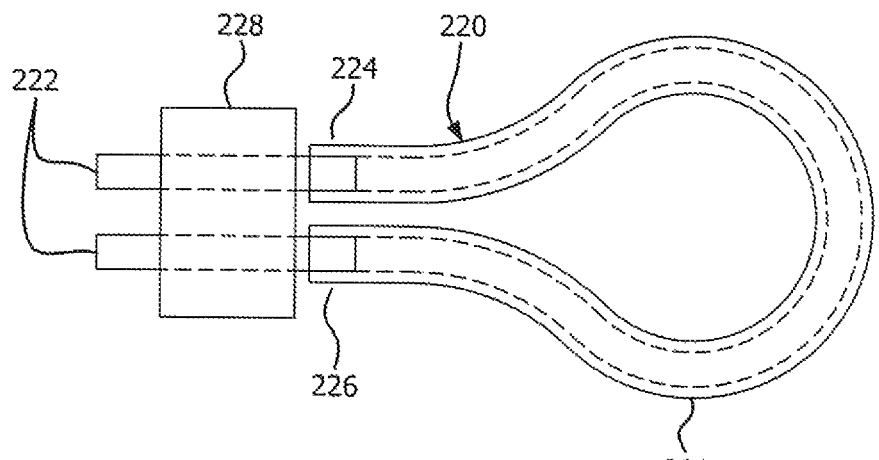
FIG. 23 is a top view of a device as described herein including a removable fitting joining two parallel ends and two resealable ports according to embodiments disclosed herein.
Figure 24:
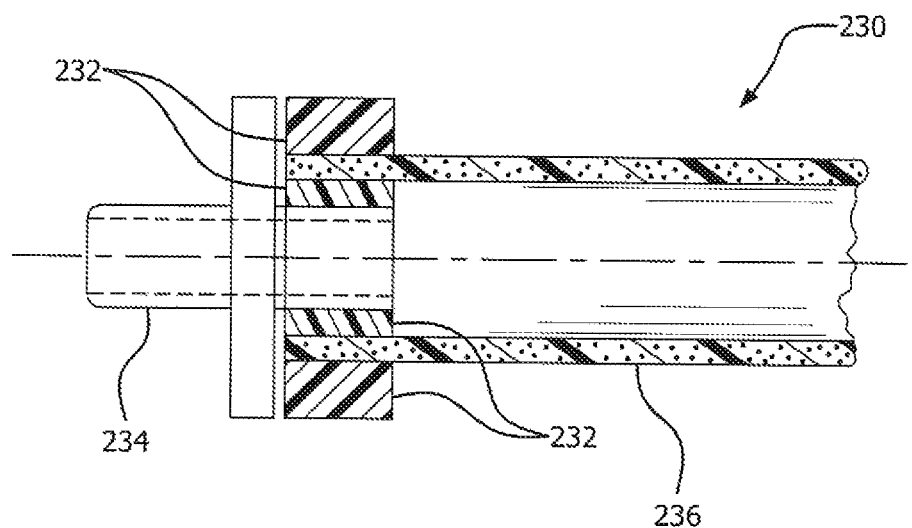
FIG. 24 is a partial view of a device as described herein including a resealable port according to embodiments disclosed herein.

In some embodiments, the step of joining the first and second ends of the implantable containment apparatus is carried out immediately after inserting the apparatus. In other embodiments, the step of joining the first and second ends is carried out a brief period of time after inserting the apparatus, for example, within one day. In other embodiments, the step of joining is carried out more than one day (e.g., more than 24 hours, more than one week, one week to one month, or more than one month) after inserting the apparatus. FIG. 23 illustrates an apparatus 220 of the present invention having resealable ports 222 at both ends 224 of a conduit 226, where the resealable ports 222 are positioned and maintained sufficiently close together with a fitting 228 so that the apparatus is implantable and accessible at a single site in a patient. The apparatus includes a spine 229 as a shaping element. FIG. 24 is a cross-sectional illustration of an apparatus 230 as described herein where an adhesive 232 is used to attach resealable port 234 to a conduit 236.

Placing and Replacing a Device in the Implantable Containment Apparatus

In some embodiments, to easily place and replace a therapeutic device in a containment apparatus as described herein, a slippery, or lubricous, surface may be present on both the exterior surface of the therapeutic device and the inner surface of the conduit of the containment apparatus. In some embodiments, the conduit is constructed from a porous PTFE material that is lubricous. In some embodiments, use of a hydrogel to form the cell exclusion zone in the apparatus makes the luminal surface of the tube even more slippery. The selectively permeable polymeric materials of most therapeutic devices are also lubricous. The lubricity permits a therapeutic device to be easily placed and replaced in an implantable containment apparatus as described herein. A therapeutic device can be manipulated in and out of an apparatus described herein with forceps and the like. In some embodiments, a containment apparatus as described herein has resealable ports at both ends of the tube, and a therapeutic device is inserted into and removed from the luminal region of a tubular apparatus with a fluid stream.

It is important to have sufficient clearance between the interior surface of the conduit of the containment apparatus and the external surface of the therapeutic device inserted into the containment apparatus. Clearance allows these components to accommodate a fluid stream during loading, retrieval, and replacement of a therapeutic device or biological moiety. In some embodiments, the selectively permeable porous polymeric material of the conduit portion of the apparatus is radially distensible. Useful radially distensible materials can stretch slightly under pressure and return to their original dimensions when the pressure is released. Very close or direct contact between the interior surface of an apparatus of the conduit of the apparatus described herein and the external surface of a therapeutic device along substantially the entire length of the therapeutic device can be achieved with this type of material.

Alternatively, in some embodiments, the inner diameter of the conduit of the apparatus may be made larger than the outer diameter of the therapeutic device the apparatus is intended to contain. When this construction is implanted, vascularized, if desired, and loaded with a therapeutic device, all, or most, areas of the conduit portion of the apparatus collapse against the therapeutic device contained therein. This results in direct contact between the interior surface of the apparatus and the external surface of the therapeutic device along substantially the entire length of the therapeutic device. Even if direct contact is not achieved, the desired result can be obtained if the space that remains between the external surface of the therapeutic device and the interior surface of the conduit of the apparatus is occupied by a material, or stagnate fluid layer, of sufficient diffusive permeability to solutes and products to maintain the necessary rate of mass transport across the wall of the tube. Useful materials for this purpose include, but are not limited to, alginate, agar, a hydrogel, or a thermoreversible gel. The apparatus is collapsed against the therapeutic device primarily by the wound healing tissues of the implantation site. Useful porous polymeric materials for either of these embodiments include those listed above, as well as, similar materials having elastomeric components incorporated therein.

In some embodiments, a biological moiety or therapeutic device may be placed in a conduit of the apparatus described herein with a fluid stream by first opening both resealable ports of the tube. In some embodiments, a device for establishing a pressurized fluid stream through the luminal region of the apparatus may be attached to one of the resealable ports of the tube. A device for receiving the fluid stream is attached to the other resealable port of the tube. A fluid stream is established in the luminal region within the conduit by causing fluid flow into the appropriate resealable port and concurrently out of the other resealable port. This can be accomplished by pumping fluid at positive pressure into one of the resealable ports. In some embodiments, to place a biological moiety or a therapeutic device in the apparatus, a biological moiety or therapeutic device is first entrained in a pressurized fluid stream and then inserted into the tube with the fluid stream. Once the biological moiety or therapeutic device is placed in the tube, the fluid stream is discontinued. In some embodiments, when the fluid stream is discontinued, the biological moiety or the exterior surface of the therapeutic device contained in the tube and the interior surface of the tube are in direct contact. The resealable ports are then closed and the assembly put to use.

In some embodiments, removal of a biological moiety or a therapeutic device from a conduit of the containment apparatus described herein may be accomplished by opening both resealable ports on the tube and attaching a device for providing a pressurized fluid stream to one of the resealable ports. A pressurized fluid stream is then established around the therapeutic device and through the luminal region of the conduit to entrain the device in the fluid stream. Once entrained in the fluid stream in the tube, the biological moiety or therapeutic device may be removed from the tube through one of the resealable port with the fluid stream. The fluid stream can either push or pull the biological moiety or the therapeutic device out of the apparatus. If desired, another biological moiety or therapeutic device can be placed in the apparatus by repeating the appropriate insertion steps outlined above. In addition to ease of insertion and retrieval of a therapeutic device contained in an apparatus as described herein, the present invention has the advantage of preserving tissues associated with the selectively permeable material of the apparatus from damage during placement and exchange of a biological moiety or a therapeutic device in the apparatus.

Care should be taken to avoid collapsing the conduit of the containment apparatus during insertion or removal of a therapeutic device. In some embodiments, maintaining internal positive pressure in a range of about 5-100 psi (i.e. about $3.45 \times 10^4$ $N/m^2$ to about $6.89 \times 10^5$ $N/m^2$) may be used to prevent collapse of the conduit during loading, unloading, and refilling of the tube with a therapeutic device. The thickness and nominal diameter of a porous conduit will depend in large part on how much internal pressure a particular containment apparatus as described herein will tolerate.

When a biological moiety or a therapeutic device is contained in a containment apparatus as described herein, the minimum permissible clearance between the exterior surface of the therapeutic device and the interior surface of the apparatus depends in large part on the particular therapeutic device embodiment and the therapy sought to be achieved with the device. For example, cell encapsulation devices implanted in a patient have a bidirectional flux of solutes between cells in the cell encapsulation device and tissues of the patient. To maintain a rate of flux sufficient to sustain the viability of the encapsulated cells and to effect the desired therapeutic result, cell encapsulation devices contained in an apparatus as described herein it is useful to have very small clearances in a range of about 0.5 microns to about 50 microns or direct contact between the permeable surface of the device and the interior surface of the containment apparatus.

In some embodiments, therapeutic devices useful in conjunction with the present invention include devices that are generally cylindrical in geometry with a flexible cell displacing core enclosed in a selectively permeable membrane. In some embodiments, the selective permeability of the membrane can be adjusted by impregnating the membrane with an appropriate hydrogel material. The cell displacing core positions the encapsulated cells in direct, or near direct, contact with the selectively permeable membrane. The encapsulated cells are positioned in the device at a distance from a nutrient source and at a cell density that minimizes the diffusion distance biochemical substances must traverse between each encapsulated cell and the external environment of the device. This configuration enables a maximum number of encapsulated cells to be maintained in a given volume at high levels of viability and productivity. The selectively permeable membrane contains cells within the device while permitting exchange of biochemical substances between the encapsulated cells and the exterior surface of the device. In a situation where the cell encapsulation device is embedded in a patient and contains allogeneic or xenogeneic cells, the selectively permeable membrane also serves to isolate the encapsulated cells from the immune system of the patient.

In some embodiments, a containment apparatus as described herein, in conjunction with cells in a cell encapsulation device can function as an implantable therapeutic product delivery system, an implantable artificial organ, or a bioreactor. In one embodiment, the apparatus described herein, in conjunction with a cell encapsulation device, may be used as an artificial organ, such as an artificial pancreas. In some embodiments, the containment apparatus as described herein enables a complete cell encapsulation device and its entire cache of cells to be easily inserted, retrieved, and replaced in the apparatus as a unit.

By maintaining the containment apparatus in a gently curved generally toroidal conformation as described herein, twisting, kinking, or other extreme bending of a therapeutic device contained therein is minimized or eliminated. Such distortion of a therapeutic device contained in an apparatus can damage the device and/or make removal of the device from an apparatus difficult or impossible.

The examples below are intended to further illustrate certain aspects of the methods and compositions described herein, and are not intended to limit the scope of the claims.

EXAMPLES

Example 1

Production of implantable apparatus: With the following method, an apparatus as described herein was made. The apparatus has a curved configuration in use. Two layers of expanded PTFE membranes each having different porosities was used to form the conduit. The portion of the laminate that was the cell exclusion zone was a layer of expanded PTFE membrane as taught in U.S. Pat. No. 5,478,589 to Bacino, et al. It was a very thin, very strong non-woven web composed substantially of fibrils in which there were essentially no nodes. This layer had an average pore size of about 0.4 microns, as measured by porometry, and a thickness of about 1 micron in its laminated, or finished, form. The portion of the laminate containing the cell permeable zone was an expanded PTFE membrane as taught in U.S. Pat. No. 5,814,405 to Branca et al. having an average pore size greater than about 5.0 microns, as measured by fibril length, and a thickness of about 30 microns.

A tubular conduit was made from this laminate by attaching two planar sheets of the laminate together along a line that defines the perimeter of the tubular form. The sheets of laminate were attached with heat and pressure using a pair of stainless steel machined dies having opposing raised tracks on each member of the die pair. To make the tubular form, two sheets of laminate were first held together in the die with their respective cell exclusion zones facing each other. A tubular core made of full density PTFE was placed between the layers of laminate within the outline of the perimeter defined by the elevated tracks prior to the heating and pressing process. Once in the die, the laminates were placed in a pneumatic press with platens pre-heated to about 370° C. for about 10 minutes at a pressure sufficient to densify the expanded FIFE membrane. When brought together under heat and pressure, the elevated opposing tracks of the dies joined the layers in the areas contacted by the raised tracks. The tube, core, and attached planar material were allowed to cool to room temperature and then removed from the die. The core was removed from the interior of the tubular portion of the apparatus by injecting water between the core and the wall of the tube with a hypodermic syringe. The joined portions of the construction formed the perimeter of the tube except at the ends, which remained open in order to receive a therapeutic device. The tube thus formed was about 5.08 cm long and an inner diameter of about 0.16 cm, with one closed and one open end. The planar material that remained attached to the apparatus after its construction was removed leaving a hollow tubular apparatus.

A resealable port was attached to both open ends of the tube as follows. Two rods made of full density PTFE were machined into hollow tubular configurations about 0.94 cm long comprising three main portions having inner diameters of about 0.1 cm. The first portion has an outer diameter of about 0.16 cm, a length of about 0.30 cm, and fits snugly inside the end of the tubular component of the apparatus. The second portion has an outer diameter of about 0.2 cm, a length of about 0.20 cm and functions as an abutment for the tube and the sealing element. The third portion had an outer diameter of about 0.16 cm, a length of about 0.30 cm and serves to receive and retain a sealing element. For each tube, a 2.0 mm nominal inner diameter piece of fluorinated ethylene propylene (FEP) shrink-tube was placed over the first portion of the resealable port, trimmed to length, and heated with a hot air gun to a temperature sufficient to shrink the FEP in place. The open ends of the above-described tubes were stretched slightly and gently placed over the FEP coated first portion of one of the resealable ports up to the second portion of the resealable port. A second piece of FEP shrink-tube was placed over the tube above the underlying FEP coated first portion of the resealable port. The second piece of FEP was heated with a hot air gun to a temperature sufficient to shrink the FEP over the tube. Hot air was also used to partially melt both the inner and the outer layers of FEP shrink-tube thereby forming a strong bond between the expanded PTFE tube and the resealable port.

Example 2

Use of implantable apparatus: An implantable containment apparatus described in Example 1 was deformed to a straight configuration and placed inside of a hollow tunneling tool. The hollow tunneling tool was used to create an arced, substantially-tubular cavity in the tissue bed. A small incision was made in a tissue bed. One end of a projection of the tunneling tool was inserted into the tissue bed through the incision at an entry point, which will become the proximal end of an arced substantially tubular tissue tract. The projection was advanced through the tissue bed, creating an arced tissue tract that exited the tissue bed through the same incision at an exit point, which was the distal end of the tissue tract. The apparatus inside the tunneling tool was grasped at the distal end of the tissue tract while the tunneling tool was retracted, leaving the implantable containment apparatus placed in the arced, substantially-tubular cavity in the tissue bed. The first end of the implantable containment apparatus exited from the distal end of the arced tissue tract near the entry point where the second end of the apparatus protruded from the proximal end of the tissue tract. The first and second ends of the implantable containment apparatus were removably joined using magnetic fittings.

Example 3

Use of implantable apparatus: A hollow tunneling tool was used to create an arced, substantially-tubular cavity in a tissue bed. The proximal and distal end of the tract were in close proximity. The tunneling tool was then retracted, leaving an arced, substantially-tubular cavity in the tissue bed.

Following the removal of the tunneling tool, the first end of the apparatus described in Example 1 was inserted through a small incision into the proximal end of the tissue tract and advanced to the distal end of the tissue tract. The first end of the apparatus exited from the distal end of the arced tissue tract near the entry point and through the same incision, where the second end of the apparatus remained protruding from the proximal end of the tissue tract. The first and second ends of the apparatus were then joined using magnetic fittings to form a generally toroidal configuration.

The invention may also be described by the following:
1. An implantable containment apparatus comprising:
 (a) a conduit comprising an exterior surface and an interior surface, wherein the interior surface defines a luminal region, the conduit having a first end comprising a first resealable port, and a second end comprising a second resealable port;
 (b) a shaping element, wherein the shaping element is configured to induce the conduit to have a curved shape,
 wherein the conduit is adapted to receive the therapeutic device into the luminal region through the first or the second resealable port.
2. The apparatus of claim 1, wherein the conduit comprises a porous material having a porosity that is sufficiently porous to permit growth of vascular tissue from a patient within the pores of the porous material.
3. The apparatus of claim 1 or 2, wherein the porous material permits growth of vascular tissue across the entire thickness of the conduit.
4. The apparatus of claim 1, 2, or 3, wherein the conduit comprises a laminate comprising a first layer adjacent to a second layer, the first layer comprising a first porous material having a first porosity that is impervious to cellular ingrowth across the interior surface of the chamber, the second layer comprising a second porous material having a second porosity that is sufficiently porous to permit growth of vascular tissue from a patient within the pores of the second porous material up to, but not through, the first layer.
5. The apparatus of any preceding claim, wherein the first or he second porous material comprises polytetrafluoroethylene.
6. The apparatus of any preceding claim, wherein the first or the second porous material comprises a bioabsorbable material.
7. The apparatus of any preceding claim, wherein the first or the second porous material comprises ePTFE and a bioabsorbable material.
8. The apparatus of any preceding claim, wherein the bioabsorbable material is in the form of a powder.
9. The apparatus of any preceding claim, wherein the shaping element comprises a shape memory material selected from shape memory alloys and shape memory polymers.
10. The apparatus of any preceding claim, wherein the shaping element is a winding, a strip, a spine, or a stent.
11. The apparatus of any preceding claim, wherein the shaping element is a length of the conduit comprising an ovoid cross-section.
12. The apparatus of any preceding claim, wherein the shaping element is at least one magnet.
13. The apparatus of any preceding claim, further comprising at least one fitting for separably joining the first end and the second end.
14. The apparatus of any preceding claim, further comprising one or more sensors.
15. A implantable containment apparatus comprising:
 a) a conduit comprising an exterior surface and an interior surface, wherein the interior surface defines a luminal region having a first end and a second end, wherein the conduit has a first configuration where the ends are unconnected and a second configuration where the ends are connected and the conduit has a curved shape; and
 b) a fitting for removably connecting the first end to the second end.
16. A method for implanting a containment apparatus in a tissue bed of a patient comprising:
 (a) inserting the containment apparatus into a substantially tubular cavity in a tissue bed, wherein the containment apparatus comprises:
 (i) a conduit comprising an exterior surface, an interior surface that defines a luminal region, a first end comprising a first resealable port, and a second end comprising a second resealable port;
 (ii) a shaping element, wherein the shaping element is configured to induce the conduit into a generally toroidal configuration;
 wherein the conduit is adapted to receive at least one therapeutic device into the luminal region through at least one of the first and second resealable ports; and
 (b) placing the apparatus into a generally toroidal configuration.
17. The method of claim 16, wherein placing the apparatus into a generally toroidal configuration comprises allowing the apparatus to migrate within the tissue bed into a generally toroidal configuration.
18. The method of claim 16 or 17, further comprising deforming the containment apparatus from a primary configuration to a deformed configuration prior to inserting the containment apparatus, wherein the primary configuration is a generally toroidal configuration.
19. The method of claim 16, 17, or 18, further comprising joining the first end and the second end.
20. The method of any preceding claim, further comprising implanting a second containment apparatus into the substantially tubular cavity.
21. The method of any preceding claim, further comprising removing the containment apparatus from the substantially tubular cavity and inserting a second containment apparatus into the substantially tubular cavity.
22. The method of any preceding claim, further comprising removing the containment apparatus via a pressurized fluid stream.
23. A method for implanting a containment apparatus in a tissue bed of a patient, comprising:

(a) inserting a first end of a containment apparatus into a curved, substantially tubular cavity in a tissue bed through an entry point in an incision in the tissue bed, wherein the containment apparatus comprises:
  (i) a conduit comprising an exterior surface, an interior surface that defines a luminal region, a first end comprising a resealable port, and a second end comprising a resealable port;
  wherein the conduit is adapted to receive at least one therapeutic device into the luminal region through at least one resealable port; and
(b) advancing the first end of the containment apparatus in a curved path through the tissue bed; and
(c) removing the first end of the containment apparatus through an exit point in the incision in the tissue bed proximate the entry point.

24. The method of claim 23, further comprising, joining the first end and the second end of the containment apparatus after removing the first end of the containment apparatus.

25. The method of claim 23 or 25, further comprising placing the apparatus into a generally toroidal configuration.

26. The method of claim 23, 24, or 25, further comprising deforming the containment apparatus from a primary configuration to a deformed configuration prior to inserting the first end of the containment apparatus into the curved, substantially tubular cavity, wherein the primary configuration is a generally toroidal configuration.

27. The method of any preceding claim, further comprising implanting a second containment apparatus into the curved, substantially tubular cavity.

28. The method of any preceding claim, further comprising removing the containment apparatus from the substantially tubular cavity and inserting a second containment apparatus into the substantially tubular cavity.

29. The method of any preceding claim, further comprising removing the containment apparatus via a pressurized fluid stream.

The compositions and methods of the appended claims are not limited in scope by the specific compositions and methods described herein, which are intended as illustrations of a few aspects of the claims and any compositions and methods that are functionally equivalent are within the scope of this disclosure. Various modifications of the compositions and methods in addition to those shown and described herein are intended to fall within the scope of the appended claims. Further, while only certain representative compositions, methods, and aspects of these compositions and methods are specifically described, other compositions and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. An implantable containment apparatus comprising:
   (a) a conduit comprising an exterior surface and an interior surface and a first end and a second end, wherein the interior surface defines a luminal region;
   (b) a shaping element configured to induce the conduit from a first configuration into a second configuration after implantation into a tissue bed and at body temperature, wherein the second configuration is a closed loop where the first end faces and abuts the second end; and
   (c) a fitting for removably connecting the first end to the second end,
   wherein the conduit is configured to receive, remove, and replace a therapeutic device or a biological moiety into the luminal region through the first end or the second end.

2. The apparatus of claim 1, wherein the conduit comprises a laminate comprising a first layer adjacent to a second layer, the first layer comprising a first porous material having a first porosity that is impervious to cellular ingrowth across the interior surface of the chamber, the second layer comprising a second porous material having a second porosity that is sufficiently porous to permit growth of vascular tissue from a patient within the pores of the second porous material up to, but not through, the first layer.

3. The apparatus of claim 2, wherein the first or the second porous material comprises polytetrafluoroethylene.

4. The apparatus of claim 2, wherein the first or the second porous material comprises a bioabsorbable material.

5. The apparatus of claim 2, wherein the first or the second porous material comprises ePTFE and a bioabsorbable material.

6. The apparatus of claim 5, wherein the bioabsorbable material is in the form of a powder.

7. The apparatus of claim 1, wherein the shaping element comprises a shape memory material selected from shape memory alloys and shape memory polymers.

8. The apparatus of claim 1, further comprising one or more sensors.

9. The apparatus of claim 1, wherein the fitting comprises a first fitting on the first end and a second fitting on the second end.

10. The apparatus of claim 9, wherein the first and second fittings are magnetic.

11. The apparatus of claim 1, wherein the body temperature is about 37° C.

12. The apparatus of claim 1, wherein the first and second ends rest in close proximity to each other.

13. The apparatus of claim 1, wherein the first and second ends are removably joined together.

14. The apparatus of claim 1, wherein the shaping element is located between layers of the conduit along the interior surface of the conduit, or a combination thereof.

15. The apparatus of claim 1, further comprising an inert core.

16. The apparatus of claim 1, wherein the conduit comprises a laminate of at least two materials having different porosities.

17. The apparatus of claim 16, wherein the at least two materials comprise at least two layers of expanded polytetrafluorethylene membrane, each said expanded polytetrafluoroethylene membrane having different porosities.

18. The apparatus of claim 1, wherein the apparatus comprises an ovoid cross-section.

19. The apparatus of claim 1, wherein the shaping element is an external winding, an external strip, an external spine, or an external stent.

20. An implantable containment apparatus comprising:
   (a) a conduit comprising an exterior surface and an interior surface and a first end and a second end, wherein the interior surface defines a luminal region;
   (b) a shaping element configured to induce the conduit from a first configuration into a second configuration after implantation and at body temperature wherein in the second configuration the first end and the second end are aligned and joined parallel to each other by a removable fitting, wherein the conduit is adapted to receive, remove, and replace a therapeutic device or a biological moiety into the luminal region through the first end or the second end, and wherein the conduit is configured to be implanted into a tissue bed.

21. The apparatus of claim 20, wherein the conduit comprises a porous material having a porosity that is sufficiently porous to permit growth of vascular tissue into the pores of the porous material.

22. The apparatus of claim 21, wherein the porous material permits growth of vascular tissue across the entire thickness of the conduit.

23. The apparatus of claim 20, wherein the conduit comprises a laminate comprising a first layer adjacent to a second layer, the first layer comprising a first porous material having a first porosity that is impervious to cellular ingrowth across the interior surface of the chamber, the second layer comprising a second porous material having a second porosity that is sufficiently porous to permit growth of vascular tissue within the pores of the second porous material up to, but not through, the first layer.

24. The apparatus of claim 20, wherein the shaping element comprises a shape memory material selected from shape memory alloys and shape memory polymers.

25. The apparatus of claim 20, wherein the shaping element is a winding, a strip, a spine, or a stent.

* * * * *